(12) United States Patent
Hwang et al.

(10) Patent No.: US 10,138,185 B1
(45) Date of Patent: Nov. 27, 2018

(54) METHOD FOR PREPARATION OF MANNITOL FROM FRUCTOSE USING BUTANOL AS SOLVENT

(71) Applicant: KOREA RESEARCH INSTITUTE OF CHEMICAL TECHNOLOGY, Daejeon (KR)

(72) Inventors: Dong Won Hwang, Daejeon (KR); Pravin Pandharinath Upare, Daejeon (KR); Young Kyu Hwang, Daejeon (KR); Do Young Hong, Gyeonggi-do (KR); Jong San Chang, Daejeon (KR); U Hwang Lee, Daejoen (KR); Su Kyung Lee, Daejeon (KR); Kyung Ho Cho, Gyeonggi-do (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 15/991,930

(22) Filed: May 29, 2018

(30) Foreign Application Priority Data

May 29, 2017 (KR) ........................ 10-2017-0066283

(51) Int. Cl.
| | | |
|---|---|---|
| *C07C 29/141* | (2006.01) | |
| *C07C 31/26* | (2006.01) | |
| *C07H 3/02* | (2006.01) | |
| *B01J 23/72* | (2006.01) | |

(52) U.S. Cl.
CPC ............. *C07C 29/141* (2013.01); *B01J 23/72* (2013.01); *C07C 31/26* (2013.01); *C07H 3/02* (2013.01)

(58) Field of Classification Search
CPC ..... C07C 31/26; C07C 29/141; C07C 29/145; C07H 3/02; B01J 21/08; B01J 21/72
See application file for complete search history.

(56) References Cited

U.S. PATENT DOCUMENTS 6,649,754 B1    11/2003    Mohr et al.

FOREIGN PATENT DOCUMENTS

| JP | 2012-041335 | 3/2012 |
| KR | 2017-0046119 | 4/1917 |
| KR | 2005-0040530 | 5/2005 |

OTHER PUBLICATIONS

Zelin et al., Selective liquid-phase hydrogenation of fructose to D-mannitol over copper-supported nanoparticles Chemical Engineering Journal (Amsterdam, Netherlands) (2017), 319, 48-56).*

* cited by examiner

*Primary Examiner* — Jafar F Parsa
(74) *Attorney, Agent, or Firm* — Norton Rose Fulbright US LLP (57) ABSTRACT

The present invention relates to a method for preparing mannitol which includes performing the hydrogenation of fructose in the presence of a Cu-based nanocomposite catalyst, for example, a nanocomposite catalyst of CuO(x)/SiO2(100-x) (wherein x is a real number from 20 to 90), using butanol as a solvent.

7 Claims, 4 Drawing Sheets

METHOD FOR PREPARATION OF MANNITOL FROM FRUCTOSE USING BUTANOL AS SOLVENT

CROSS REFERENCE TO RELATED APPLICATIONS

This application claims priority to and the benefit of Korean Patent Application No. 10-2017-0066283, filed May 29, 2017. The contents of the referenced application are incorporated into the present application by reference.

BACKGROUND OF THE INVENTION

Field of the Invention

The present invention relates to a method for preparing mannitol which includes performing the hydrogenation of fructose in the presence of a CuO(x)/SiO2(100-x) catalyst (in which x is a real number from 20 to 90) using butanol as a solvent.

Description of Related Art

Mannitol was discovered by Joseph Louis Proust in 1806. It is on the World Health Organization's list of essential drugs and is one of the most effective and safe medicines required in a health system. It was originally made from the flowering ash and called manna due to its supposed resemblance to the Biblical food.

Mannitol, which is a hexose sugar alcohol, is contained in brown algae, mushrooms, fungi, etc. in nature. Having a sweetness level of 30% to 40% of sugar, mannitol is not only used as a substitute sweetener in food production where the use of sugar is limited, but is also widely used as an additive for confectioneries, a filler for pharmaceuticals, a surfactant, and a waterproofing agent, etc. due to its excellent properties such as cold taste, low hygroscopicity, fluidity, etc. Mannitol is widely used in the food and pharmaceutical industries; for example, it is used as an intermediate of antihypertensive agents and is also used as a coating agent to reduce bitter taste in the manufacturing process of various pharmaceutical preparations.

Specifically, being poorly absorbed in the intestines, mannitol, which is a saccharide, is used as a sweetener in diabetic diets. As a drug, mannitol is also used to lower the high intraocular pressure observed in glaucoma or lower increased intracranial pressure. Medically, mannitol can be administered by injection, and its effect usually begins to appear within 15 minutes and lasts up to 8 hours.

Additionally, since mannitol has a low absorption rate and contains fewer calories than sugar, it is widely used as a food additive for diet and as an excipient for medicines.

Mannitol is naturally present in many fruits and vegetables, but only in trace amounts. Therefore, it is not economically viable to extract it from fruits or vegetables. Additionally, mannitol can also be produced by biosynthesis, such as fermentation by microorganisms. The microorganisms involved in the production of mannitol include: yeasts, such as *Candida zeylannoide, Candida lipolitica, Cryptococcus neoformans, Torulopsis mannitofaciens*, etc.; bacteria, such as *Lactobacillus brevis, Leuconostoc mesenteriode, Mycobacterium smegmatis*, etc.; and fungi, such as *Mucor rouxii, Aspergillus nidulans, Penicillum scabrosum*, etc. The method using microorganisms can specifically produce only mannitol from glucose or fructose, which can significantly ease the process of separation and purification of mannitol after the reaction, but the method has difficulty in industrialization due to the low productivity or yield of mannitol.

Furthermore, mannitol may be commercially produced by chemical synthesis. However, although mannitol may be chemically prepared through a catalytic reaction by separating fructose from sugar, etc. by hydrolysis and adding hydrogen to the fructose under high-temperature and high-pressure conditions, in conventional processes, mannitol yield is low, and a large amount of sorbitol is produced as a by-product, thus requiring a separate purification process, resulting in high production cost. In addition, the conventional methods have disadvantages in that there is a risk because the reaction is performed under high-temperature, high-pressure conditions, and there is a burden with regard to waste disposal.

For example, U.S. Pat. No. 6,649,754 discloses a method for preparing mannitol using a Raney copper catalyst (Al: 39 wt %; Cu: 61 wt %). However, this method has disadvantages in that the reaction must be performed at a high pressure of 170 bar even at 110° C., and in particular, the yields of mannitol and sorbitol are 63% and 35%, respectively, and thus the yield and selectivity are still low.

SUMMARY OF THE INVENTION

The present inventors have made efforts to develop a method capable of preparing mannitol from fructose with high yield and/or selectivity under mild conditions. As a result, they have confirmed that when the hydrogenation of fructose is performed using a Cu-based nanocomposite catalyst and butanol as a solvent, mannitol can be produced with high yield and selectivity under mild conditions of 100 bar or less compared to when other solvents are used, and also that the problem of leaching of copper metal during the reaction can be solved, thereby completing the present invention.

To achieve the above objects, an aspect of the present invention provides a method for preparing mannitol, which includes performing the hydrogenation of fructose in the presence of a Cu-based nanocomposite catalyst, for example, a CuO(x)/SiO2(100-x) catalyst (in which x is a real number from 20 to 90), using butanol as a solvent.

The present invention is based on the discovery that, in producing high value-added mannitol by the hydrogenation of fructose using a catalyst, mannitol can be produced with high yield and selectivity when a catalyst containing copper is used in a predetermined amount and butanol is used as a solvent.

In particular, as the butanol to be used as the solvent, n-butanol, 2-butanol, or isobutanol may be used alone or in a combination of two or more.

In the method for preparing mannitol according to the present invention, the hydrogenation may be performed at 80° C. to 180° C. Specifically, the hydrogenation may be performed at a temperature of 100° C. to 150° C. or 130° C. to 170° C., but the reaction temperature is not limited thereto. When the temperature is below 80° C., the reaction may not continue to completion, and thus the fructose conversion and/or mannitol yield may be lowered. In contrast, when the temperature is above 180° C., undesirable reactions may occur as well, thus lowering the selectivity for mannitol.

In the method for preparing mannitol according to the present invention, the hydrogenation may be performed at a pressure of 10 bar to 100 bar. Specifically, the hydrogenation may be performed at a pressure of 20 bar to 70 bar or at a pressure of 25 bar to 50 bar. When the pressure is below 10 bar, the reaction may not occur at all or may not continue to completion, and thus the conversion of fructose and/or mannitol yield may be lowered. In contrast, when the pressure is above 100 bar, expensive equipment may be required to achieve the reaction conditions or the energy cost may increase, thereby increasing the process cost.

In the method for preparing mannitol according to the present invention, the hydrogenation may be performed for 3 to 24 hours. Specifically, the hydrogenation may be performed for 5 to 15 hours, and more specifically 7 to 12 hours, but the time for hydrogenation is not limited thereto. When the hydrogenation is performed for less than 3 hours, the reaction may not continue to completion, and thus the conversion of fructose and/or mannitol yield may be lowered. In contrast, when the hydrogenation is performed for more than 24 hours, the reaction is already complete and unnecessary processes continue, and thus undesired reactions increase and the mannitol selectivity may be lowered.

The temperature, pressure, and time conditions of the hydrogenation may be selected in combination with mutual complementarity so as to achieve high mannitol yield and selectivity. For example, when the hydrogenation is performed under high temperature and/or pressure, it may rapidly complete within a short period of time, and thus the hydrogenation can be performed for a relatively short period of time.

In the method for preparing mannitol according to the present invention, the catalyst may be used in an amount of 5 wt % to 100 wt % relative to the weight of fructose. Specifically, the catalyst may be used in an amount of 10 wt % to 80 wt % or 15 wt % to 70 wt % relative to the weight of fructose, but the amount of the catalyst is not limited thereto. However, when the amount of the catalyst relative to the weight of fructose is below 5 wt %, the reactants cannot sufficiently make contact with the catalyst, and thus the reaction rate may be slowed, and accordingly, biomass conversion and yield of the product may be lowered. Additionally, when the amount of the catalyst relative to the weight of fructose is higher than 100 wt %, undesirable reactions may increase, and thereby the selectivity of mannitol may be lowered.

In the method for preparing mannitol according to the present invention, the CuO(x)/SiO2(100-x) catalyst may be a Cu-based catalyst, in which x is in the range of 20 to 90, (i.e., the CuO content in the catalyst is in the range of 20 wt % to 90 wt %). Specifically, among the catalysts, the catalyst in which the CuO content is in the range of 20 wt % to 90 wt %, and more specifically, the catalyst in which the CuO content is in the range of 40 wt % to 80 wt % may be used, but the catalyst is not limited thereto. However, when the CuO content is below 20 wt % (i.e., x is below 20), not only may the conversion of fructose itself be low, but also both the yield and selectivity of mannitol may be lowered.

In the method for preparing mannitol according to the present invention, the fructose may be used in an amount of 1 wt % to 40 wt % relative to butanol, which is the solvent. Specifically, the fructose may be used in an amount of 3 wt % to 30 wt % or 5 wt % to 20 wt % relative to butanol, which is the solvent, but the amount of the fructose is not limited thereto. However, when the fructose as a reactant is used at a high concentration greater than 40 wt %, the fructose may not be completely dissolved in the solvent, or the viscosity of the solution or the density of the reactant in the solution may be high, and thus the reactant may remain unreacted without reacting sufficiently with the catalyst, thereby lowering the conversion. In contrast, when the fructose concentration is as low as less than 1 wt %, the productivity will be low, and thus the overall process efficiency may be lowered.

In an embodiment of the present invention, it was confirmed that the fructose conversion can maximally reach 100% and mannitol yield can maximally reach 94% even under mild conditions when butanol is used as a solvent in the presence of the CuO(x)/SiO2(100-x) (in which x is in the range of 20 to 90) catalyst. Additionally, it was confirmed that mannitol can be prepared with significantly higher yield and/or selectivity compared to when a different kind of catalyst is used or solvents other than butanol are used.

The mannitol prepared according to the preparation method of the present invention may be obtained in a crystallized form by cooling a mixed filtrate where mannitol, sorbitol, and a solvent are mixed, followed by separation thereof. The cooling temperature and time may be appropriately determined by those skilled in the art depending on the type of solvent used and the reaction conditions. Additionally, any known method capable of separating mannitol from a filtrate may be freely selected and used without limitation.

In an embodiment of the present invention, crystallized mannitol was separated by cooling the mannitol/sorbitol/butanol filtrate, and upon analysis of the crystallized mannitol by liquid chromatography, it was confirmed that the purity of mannitol was over 99%. That is, high-purity mannitol can be effectively prepared using the preparation method of the present invention.

The fructose used as a raw material in the method for preparing mannitol according to the present invention may be prepared by isomerization of glucose. Glucose, a hexose, is a cheap and abundant biomass resource that can be obtained from nature and can be converted to fructose by an isomerization reaction, and it is a material that can be obtained by hydrolyzing other natural biomass such as cellulose, lignocelluloses, etc. The isomerization reaction for preparing fructose from glucose can be performed using an enzyme or by a reaction using a catalyst, but the method is not limited thereto.

For example, in a previous patent application (KR Patent Application No. 10-2017-0046119) of the present inventors, it was disclosed that not only it is possible to produce fructose by isomerization of glucose in the presence of a solid base catalyst or solid acid catalyst, but also, it is possible to selectively remove crystallized unreacted glucose as well as the used solid catalyst through the process of simple cooling and filtration using the difference in solubility between glucose and fructose in butanol. As in the reaction of preparing mannitol from fructose of the present invention, the method for preparing fructose from glucose disclosed in the previous patent application also uses butanol as a solvent, and thus, the method may continuously use the filtrate, from which the catalyst used for isomerization and unreacted glucose are removed, as a raw material for the method for preparing mannitol of the present invention. For process efficiency, a process of concentration according to the fructose content in the filtrate may be further included, but the method is not limited thereto.

The preparation process using butanol and a Cu-based catalyst of the present invention, in preparing mannitol by hydrogenation of fructose using the Cu-based nanocomposite catalyst, uses butanol as a solvent, and thus higher yield and selectivity of mannitol can be achieved under mild conditions compared to processes using other solvents.

DETAILED DESCRIPTION OF THE INVENTION

Hereinafter, the present invention will be described in more detail with reference to the following Examples. However, these Examples are for illustrative purposes only and the scope of the invention is not limited by these Examples.

Preparation Example 1: Preparation of CuO(50)/SiO2 Catalyst

To 500 mL of distilled water was added 3.48 g of colloidal silica sol (Ludox SM-30, 30 wt %), and then 3.20 g of Cu(NO3)2.3H2O was slowly added thereto and mixed while stirring and maintaining the temperature at 4° C. The resulting reaction mixture was adjusted to have a pH of 9.2 by slowly adding 0.1 N NaOH thereto while stirring, maintained at room temperature for 12 hours, and reacted at 75° C. for 5 hours with stirring so as to form a precipitate. The reaction mixture was cooled to room temperature, filtrated to recover the precipitate, washed with distilled water (1,000 mL) until no sodium ion was detected, and dried at 100° C. for 12 hours, and the precipitate was obtained in the form of powder. The obtained powder was calcined at 550° C. under an air atmosphere for 5 hours and thereby a CuO(50)/SiO2 nanocomposite catalyst was obtained. The CuO(50)/SiO2 nanocomposite catalyst (1.0 g) was added into a fixed bed reactor and reduced at 290° C. using 10% hydrogen gas for 5 hours, and the resultant was used for the hydrogenation of fructose.

Preparation Example 2: Preparation of CuO(40)/SiO2 Catalyst

The CuO(40)/SiO2 nanocomposite catalyst was prepared by performing a reaction in the same manner as in Preparation Example 1 except that the amount of Cu(NO3)2.3H2O used was reduced to 2.10 g. The CuO(40)/SiO2 nanocomposite catalyst was reduced and the resultant was used for the hydrogenation of fructose.

Preparation Example 3: Preparation of CuO(60)/SiO2 Catalyst

The CuO(60)/SiO2 nanocomposite catalyst was prepared by performing a reaction in the same manner as in Preparation Example 1 except that the amount of Cu(NO3)2.3H2O used was increased to 4.8 g. The CuO(60)/SiO2 nanocomposite catalyst was reduced and the resultant was used for the hydrogenation of fructose.

Preparation Example 4: Preparation of CuO(80)/SiO2 Catalyst

The CuO(80)/SiO2 nanocomposite catalyst was prepared by performing a reaction in the same manner as in Preparation Example 1 except that the amount of Cu(NO3)2.3H2O used was increased to 12.5 g. The CuO(80)/SiO2 nanocomposite catalyst was reduced and the resultant was used for the hydrogenation of fructose.

Example 1: Preparation of Mannitol from Fructose (1)

Fructose (5 g) was mixed with 1-butanol (45 g) and the CuO(50)/SiO2 catalyst (1 g) prepared according to Preparation Example 1, heated at 120° C., charged with hydrogen gas at a pressure of 25 bar, and reacted for 5 hours to prepare mannitol. After the reaction, the CuO(50)/SiO2 catalyst was separated from the reaction mixture solution by filtration. The filtrate from which the catalyst was removed was analyzed by liquid chromatography. In particular, fructose conversion was 77%, mannitol yield was 50%, and sorbitol yield was 2%.

Example 2: Preparation of Mannitol from Fructose (2)

Fructose (5 g) was mixed with 1-butanol (45 g) and the CuO(50)/SiO2 catalyst (1 g) prepared according to Preparation Example 1, heated at 120° C., charged with hydrogen gas at a pressure of 25 bar, and reacted for 8 hours to prepare mannitol. After the reaction, the CuO(50)/SiO2 catalyst was separated from the reaction mixture solution by filtration. The filtrate from which the catalyst was removed was analyzed by liquid chromatography. In particular, fructose conversion was 89%, mannitol yield was 62%, and sorbitol yield was 14%.

Example 3: Preparation of Mannitol from Fructose (3)

Fructose (5 g) was mixed with 1-butanol (45 g) and the CuO(50)/SiO2 catalyst (1 g) prepared according to Preparation Example 1, heated at 120° C., charged with hydrogen gas at a pressure of 25 bar, and reacted for 10 hours to prepare mannitol. After the reaction, the CuO(50)/SiO2 catalyst was separated from the reaction mixture solution by filtration. The filtrate from which the catalyst was removed was analyzed by liquid chromatography. In particular, fructose conversion was 98%, mannitol yield was 70%, and sorbitol yield was 17%.

Example 4: Preparation of Mannitol from Fructose (4)

Fructose (5 g) was mixed with 1-butanol (45 g) and the CuO(50)/SiO2 catalyst (1 g) prepared according to Preparation Example 1, heated at 120° C., charged with hydrogen gas at a pressure of 30 bar, and reacted for 10 hours to prepare mannitol. After the reaction, the CuO(50)/SiO2 catalyst was separated from the reaction mixture solution by filtration. The filtrate from which the catalyst was removed was analyzed by liquid chromatography. In particular, fructose conversion was 100%, mannitol yield was 73%, and sorbitol yield was 17%.

Example 5: Preparation of Mannitol from Fructose (5)

Fructose (5 g) was mixed with 1-butanol (45 g) and the CuO(50)/SiO2 catalyst (1 g) prepared according to Preparation Example 1, heated at 120° C., charged with hydrogen gas at a pressure of 35 bar, and reacted for 10 hours to prepare mannitol. After the reaction, the CuO(50)/SiO2 catalyst was separated from the reaction mixture solution by filtration. The filtrate from which the catalyst was removed was analyzed by liquid chromatography. In particular, fructose conversion was 100%, mannitol yield was 77%, and sorbitol yield was 17%.

Example 6: Preparation of Mannitol from Fructose (6)

Fructose (5 g) was mixed with 1-butanol (45 g) and the CuO(50)/SiO2 catalyst (1 g) prepared according to Preparation Example 1, heated at 120° C., charged with hydrogen gas at a pressure of 50 bar, and reacted for 10 hours to prepare mannitol. After the reaction, the CuO(50)/SiO2 catalyst was separated from the reaction mixture solution by filtration. The filtrate from which the catalyst was removed was analyzed by liquid chromatography. In particular, fructose conversion was 100%, mannitol yield was 82%, and sorbitol yield was 17%.

Example 7: Preparation of Mannitol from Fructose (7)

Fructose (5 g) was mixed with 1-butanol (45 g) and the CuO(40)/SiO2 catalyst (1 g) prepared according to Preparation Example 2, heated at 120° C., charged with hydrogen gas at a pressure of 35 bar, and reacted for 10 hours to prepare mannitol. After the reaction, the CuO(40)/SiO2 catalyst was separated from the reaction mixture solution by filtration. The filtrate from which the catalyst was removed was analyzed by liquid chromatography. In particular, fructose conversion was 96%, mannitol yield was 75%, and sorbitol yield was 14%.

Example 8: Preparation of Mannitol from Fructose (8)

Fructose (5 g) was mixed with 1-butanol (45 g) and the CuO(60)/SiO2 catalyst (1 g) prepared according to Preparation Example 3, heated at 120° C., charged with hydrogen gas at a pressure of 35 bar, and reacted for 10 hours to prepare mannitol. After the reaction, the CuO(60)/SiO2 catalyst was separated from the reaction mixture solution by filtration. The filtrate from which the catalyst was removed was analyzed by liquid chromatography. In particular, fructose conversion was 100%, mannitol yield was 81%, and sorbitol yield was 16%.

Example 9: Preparation of Mannitol from Fructose (9)

Figure 1:
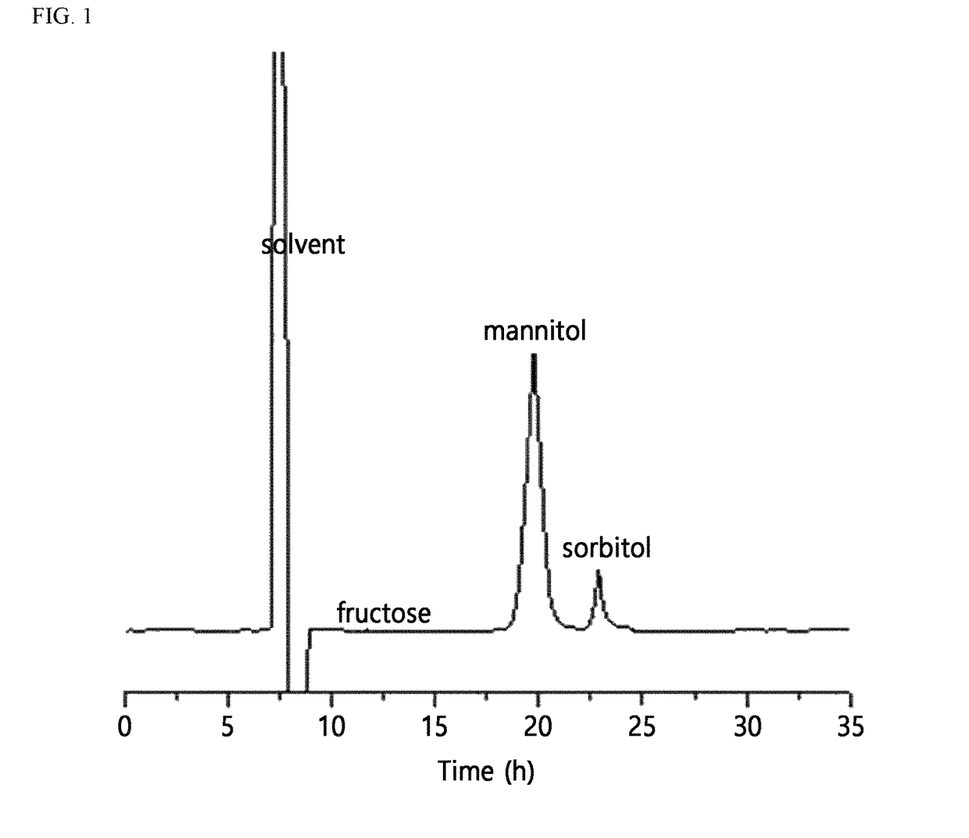
FIG. 1 shows the measurement results of liquid chromatography after the preparation of mannitol from fructose according to Example 9 of the present invention.

Fructose (5 g) was mixed with 1-butanol (45 g) and the CuO(80)/SiO2 catalyst (1 g) prepared according to Preparation Example 4, heated at 120° C., charged with hydrogen gas at a pressure of 35 bar, and reacted for 10 hours to prepare mannitol. After the reaction, the CuO(80)/SiO2 catalyst was separated from the reaction mixture solution by filtration. The filtrate from which the catalyst was removed was analyzed by liquid chromatography. The results of liquid chromatography obtained are shown in FIG. 1. In particular, fructose conversion was 100%, mannitol yield was 83%, and sorbitol yield was 15%.

Example 10: Preparation of Mannitol from Fructose (10)

Fructose (2.5 g) was mixed with 1-butanol (47.5 g) and the CuO(80)/SiO2 catalyst (1 g) prepared according to Preparation Example 4, heated at 120° C., charged with hydrogen gas at a pressure of 35 bar, and reacted for 10 hours to prepare mannitol. After the reaction, the CuO(80)/SiO2 catalyst was separated from the reaction mixture solution by filtration. The filtrate from which the catalyst was removed was analyzed by liquid chromatography. In particular, fructose conversion was 100%, mannitol yield was 93%, and sorbitol yield was 5%.

Example 11: Preparation of Mannitol from Fructose (11)

Fructose (2.5 g) was mixed with 1-butanol (47.5 g) and the CuO(80)/SiO2 catalyst (1.5 g) prepared according to Preparation Example 4, heated at 120° C., charged with hydrogen gas at a pressure of 35 bar, and reacted for 10 hours to prepare mannitol. After the reaction, the CuO(80)/SiO2 catalyst was separated from the reaction mixture solution by filtration. The filtrate from which the catalyst was removed was analyzed by liquid chromatography. In particular, fructose conversion was 100%, mannitol yield was 94%, and sorbitol yield was 4%.

Example 12: Preparation of Mannitol from Fructose (12)

Fructose (7.5 g) was mixed with 1-butanol (42.5 g) and the CuO(80)/SiO2 catalyst (1.5 g) prepared according to Preparation Example 4, heated at 160° C., charged with hydrogen gas at a pressure of 35 bar, and reacted for 10 hours to prepare mannitol. After the reaction, the CuO(80)/SiO2 catalyst was separated from the reaction mixture solution by filtration. The filtrate from which the catalyst was removed was analyzed by liquid chromatography. In particular, fructose conversion was 100%, mannitol yield was 80%, and sorbitol yield was 17%.

Example 13: Preparation of Mannitol from Fructose (13)

Fructose (7.5 g) was mixed with 1-butanol (42.5 g) and the CuO(80)/SiO2 catalyst (1.5 g) prepared according to Preparation Example 4, heated at 160° C., charged with hydrogen gas at a pressure of 50 bar, and reacted for 10 hours to prepare mannitol. After the reaction, the CuO(80)/SiO2 catalyst was separated from the reaction mixture solution by filtration. The filtrate from which the catalyst was removed was analyzed by liquid chromatography. In particular, fructose conversion was 100%, mannitol yield was 85%, and sorbitol yield was 13%.

Example 14: Preparation of Mannitol from Fructose

Figure 4:
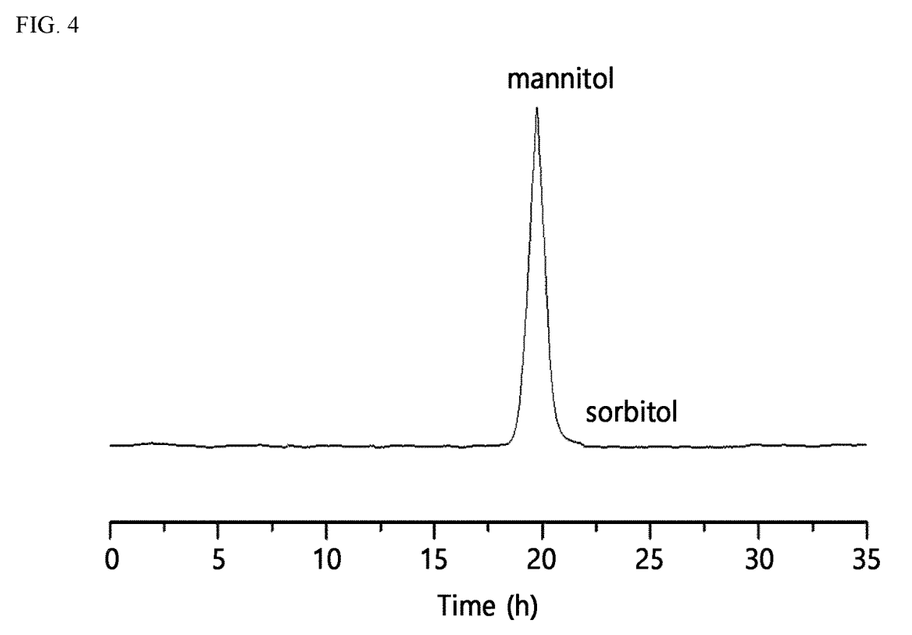
FIG. 4 shows the measurement results of liquid chromatography after the preparation of mannitol from fructose using 1-butanol as a solvent according to Example 14 of the present invention.

The filtrate obtained in Example 13, in which mannitol/sorbitol/butanol were mixed and the CuO(80)/SiO2 catalyst was separated, was cooled to room temperature, and the crystallized mannitol was separated from the filtrate by filtration. As a result of the analysis of the obtained mannitol, it was confirmed that the separated mannitol had a purity of 99% or higher (FIG. 4). From these results, it was confirmed that high-purity mannitol can be prepared by the preparation method of the present invention.

Figure 2:
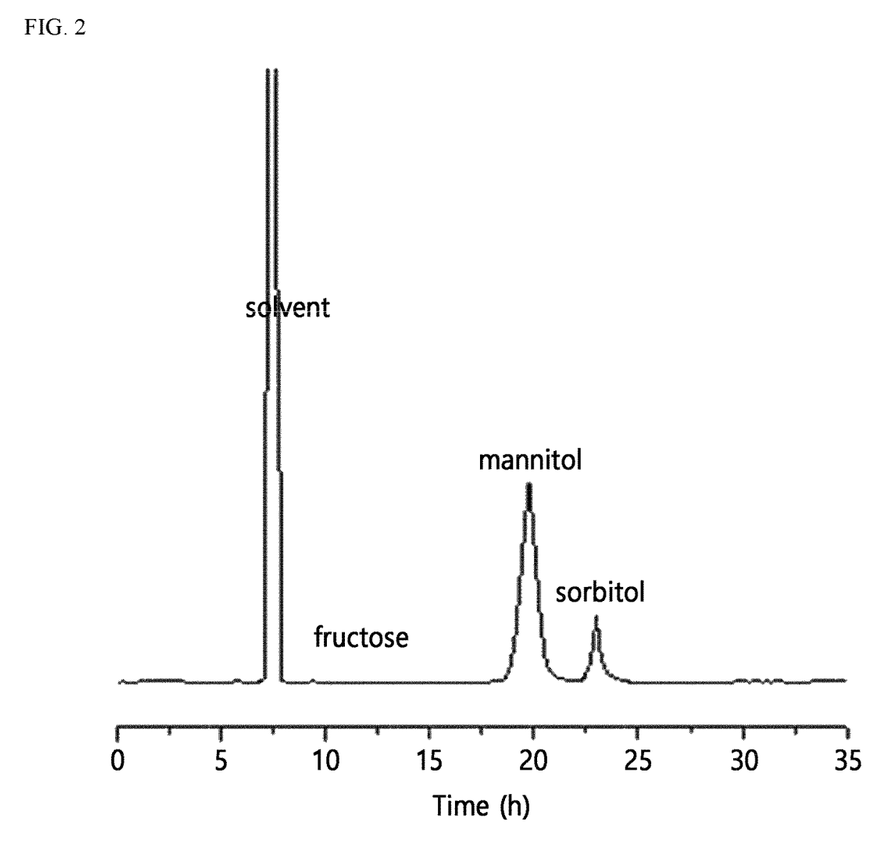
FIG. 2 shows the measurement results of liquid chromatography after the preparation of mannitol from fructose using water as a solvent according to Comparative Example 1 of the present invention.

Comparative Example 1: Preparation of Mannitol from Fructose Using Water as Solvent Fructose (5 g) was mixed with water (45 g) and the CuO(50)/SiO2 catalyst (1 g) prepared according to Preparation Example 1, heated at 120° C., charged with hydrogen gas at a pressure of 25 bar, and reacted for 6 hours to prepare mannitol. After the reaction, the CuO(50)/SiO2 catalyst was separated from the reaction mixture solution by filtration. The filtrate from which the catalyst was removed was analyzed by liquid chromatography. The results of liquid chromatography obtained are shown in FIG. 2. In particular, fructose conversion was 100%, mannitol yield was 43%, and sorbitol yield was 18%.

Figure 3:
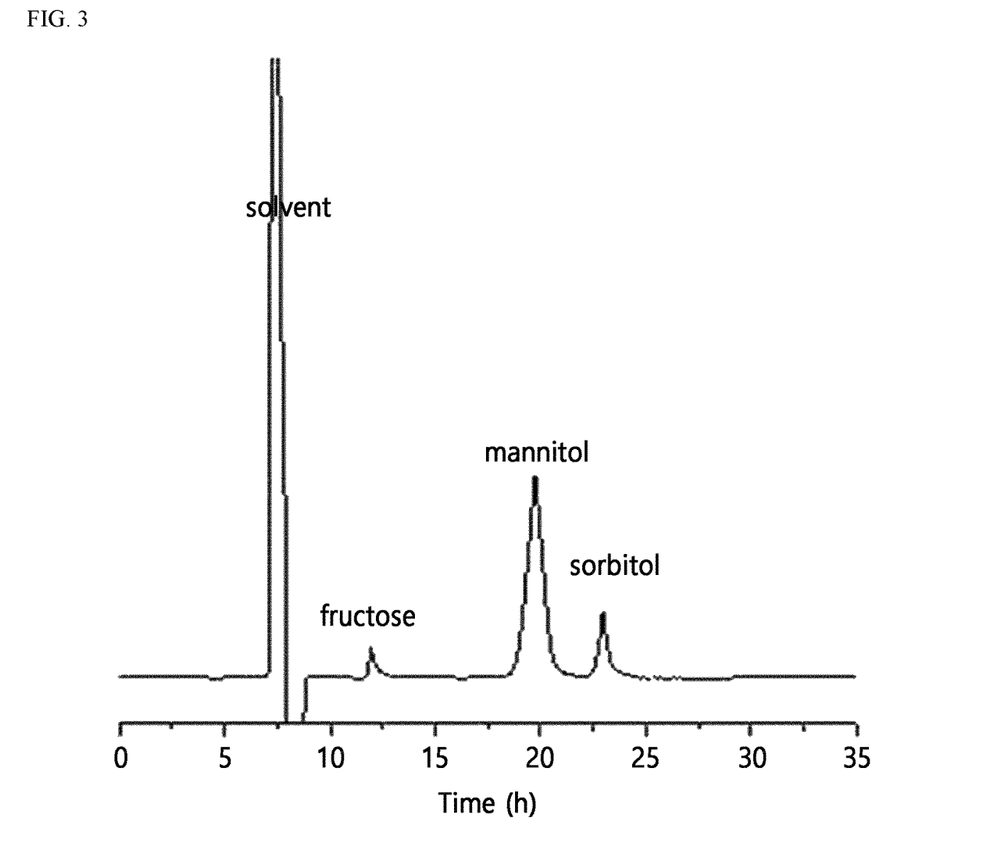
FIG. 3 shows the measurement results of liquid chromatography after the preparation of mannitol from fructose using ethanol as a solvent according to Comparative Example 2 of the present invention.

Comparative Example 2: Preparation of Mannitol from Fructose Using Ethanol as Solvent Fructose (5 g) was mixed with ethanol (45 g) and the CuO(50)/SiO2 catalyst (1 g) prepared according to Preparation Example 1, heated at 120° C., charged with hydrogen gas at a pressure of 25 bar, and reacted for 6 hours to prepare mannitol. After the reaction, the CuO(50)/SiO2 catalyst was separated from the reaction mixture solution by filtration. The filtrate from which the catalyst was removed was analyzed by liquid chromatography. The results of liquid chromatography obtained are shown in FIG. 3. In particular, fructose conversion was 97%, mannitol yield was 51%, and sorbitol yield was 18%.

Comparative Example 3: Preparation of Mannitol from Fructose Using Copper-Chromite Catalyst Cu-chromite (CuO—Cr2O3) powder (1.0 g) was added into a fixed bed reactor and reduced at 290° C. for 5 hours using 10% hydrogen gas.

Fructose (5 g) was mixed with ethanol (45 g) and the reduced copper-chromite catalyst (1.0 g), heated at 120° C., charged with hydrogen gas at a pressure of 35 bar, and reacted for 10 hours to prepare mannitol. After the reaction, the Cu-chromite catalyst was separated from the reaction mixture solution by filtration. The filtrate from which the catalyst was removed was analyzed by liquid chromatography. In particular, fructose conversion was 100%, mannitol yield was 51%, and sorbitol yield was 3%.

Comparative Example 4: Preparation of Mannitol from Fructose Using CuO(10)/SiO2 Catalyst The CuO(10)/SiO2 nanocomposite catalyst was prepared in the same manner as in Preparation Example 1 except that the amount of Cu(NO3)2.3H2O used was reduced to 0.36 g. The CuO(10)/SiO2 nanocomposite catalyst was reduced to prepare the CuO(10)/SiO2 catalyst for the hydrogenation of fructose.

Fructose (5 g) was mixed with ethanol (45 g) and the CuO(10)/SiO2 catalyst (1.0 g) prepared as described above, heated at 120° C., charged with hydrogen gas at a pressure of 35 bar, and reacted for 10 hours to prepare mannitol. After the reaction, the CuO(10)/SiO2 catalyst was separated from the reaction mixture solution by filtration. The filtrate from which the catalyst was removed was analyzed by liquid chromatography. In particular, fructose conversion was 70%, mannitol yield was 50%, and sorbitol yield was 25%.

Comparative Example 5: Preparation of Mannitol from Fructose Using Ru(1.4 wt %)-Sn(3.3 wt %)/ZnO Catalyst 0.1 M Zn(NO3)2.6H2O and 1.0 M SnCl4.5H2O solutions were simultaneously added dropwise to water (200 mL) and the mixture was adjusted to have a pH of 7.5. Upon precipitation, the solution was stirred at room temperature for 12 hours. 0.5 M RuCl3.xH2O was added dropwise to the mixed solution and NaOH was continuously added thereto to maintain its pH at 7.2. The mixed solution was stirred at room temperature for 5 hours and left at 85° C. for 5 hours.

The reaction mixture was cooled to room temperature and the precipitate was recovered by filtration and washed with distilled water (1,000 mL) until no sodium ion was detected. The resultant was dried at 100° C. for 12 hours and the precipitate was obtained in the form of powder.

The obtained powder (1.0 g) was added into a fixed bed reactor and reduced at 400° C. for 5 hours using 10% hydrogen gas and the resultant was used for the hydrogenation of fructose.

Fructose (5 g) was mixed with ethanol (45 g) and the Ru(1.4 wt %)-Sn(3.3 wt %)/ZnO catalyst (1.0 g) prepared as described above, heated at 120° C., charged with hydrogen gas at a pressure of 35 bar, and reacted for 10 hours to prepare mannitol. After the reaction, the Ru(1.4 wt %)-Sn (3.3 wt %)/ZnO catalyst was separated from the reaction mixture solution by filtration. The filtrate from which the catalyst was removed was analyzed by liquid chromatography. In particular, fructose conversion was 74%, mannitol yield was 56%, and sorbitol yield was 12%.

Comparative Example 6: Preparation of Mannitol from Fructose Using CuO(80)/ZnO Catalyst Cu(NO3)2.3H2O (48.7 g) and Zn(NO3)2.6H2O (15.0 g) were added to distilled water (400 mL) at room temperature to prepare a precursor solution. The obtained aqueous precursor solution was adjusted to have a pH of 6.5 by adding NaOH (0.2 M) while stirring, maintained at room temperature for 12 hours, and reacted at 65° C. for 5 hours, and thereby a precipitate was formed.

The reaction mixture was cooled to room temperature and the precipitate was recovered by filtration and washed with distilled water (1,000 mL) until no sodium ion was detected. The resultant was dried at 100° C. for 12 hours and the precipitate was obtained in the form of powder.

The obtained powder was calcined at 350° C. under an air atmosphere for 4 hours and thereby a CuO(80)/ZnO catalyst was obtained. The CuO(80)/ZnO catalyst (1.0 g) was added into a fixed bed reactor and reduced at 250° C. using 10% hydrogen gas for 2 hours, and the resultant was used for the hydrogenation of fructose.

Fructose (5 g) was mixed with ethanol (45 g) and the CuO(80)/ZnO catalyst (1.0 g) prepared as described above, heated at 120° C., charged with hydrogen gas at a pressure of 35 bar, and reacted for 10 hours to prepare mannitol. After the reaction, the CuO(80)/ZnO catalyst was separated from the reaction mixture solution by filtration. The filtrate from which the catalyst was removed was analyzed by liquid chromatography. In particular, fructose conversion was 100%, mannitol yield was 85%, and sorbitol yield was 11%.

As described above, the CuO(80)/ZnO catalyst showed high fructose conversion and mannitol yield. However, as a result of metal element analysis for the reaction solution, it was confirmed that Cu content was 0.04 wt % and Zn content was 0.01 wt %, and these results indicate that the stability of the CuO(80)/ZnO catalyst in the above reaction conditions is very low.

Comparing the results of Examples and Comparative Examples described above, mannitol was produced with higher yield and selectivity (reduced sorbitol yield) than fructose when the catalyst and reaction conditions are similar and when 1-butanol is used as a solvent instead of water or ethanol. In particular, mannitol could be produced in significantly high yield when the CuO/SiO2 catalyst containing CuO was used in a predetermined amount, compared to when the catalyst containing no or a low amount of copper was used (Comparative Example 4).

Additionally, when Cu-chromite (Comparative Example 3) or CuO/ZnO (Comparative Example 6) was used as the catalyst, although these catalysts contain copper, they had problems in that they could not maintain copper particles at the nanosize level or could not form nanocomposites with a carrier, and thus the mannitol yield was low or the stability of the catalysts themselves was remarkably low. Furthermore, in the case of the Cu-chromite catalyst, the catalyst contains chromium metal, which is harmful to humans, and considering that the mannitol produced therefrom is to be ingested by individuals, the Cu-chromite catalyst is not a suitable catalyst.

The invention claimed is:

1. A method for preparing mannitol, comprising performing hydrogenation of fructose in the presence of a nano-composite catalyst of $CuO(x)/SiO_2(100-x)$ (wherein x is a real number from 20 to 90) using butanol as a solvent.

2. The method of claim 1, wherein the butanol is n-butanol, 2-butanol, isobutanol, or a mixture thereof.

3. The method of claim 1, wherein the hydrogenation is performed at a temperature of 80° C. to 180° C.

4. The method of claim 1, wherein the hydrogenation is performed at a pressure of 10 bar to 100 bar.

5. The method of claim 1, wherein the catalyst is used in an amount of 5 wt % to 100 wt % relative to the weight of fructose.

6. The method of claim 1, wherein the fructose is used in an amount of 1 wt % to 40 wt % relative to the weight of butanol as a solvent.

7. The method of claim 1, wherein the fructose is prepared by the isomerization reaction of glucose.

\* \* \* \* \*